US009351695B2

(12) United States Patent
Wang et al.

(10) Patent No.: US 9,351,695 B2
(45) Date of Patent: May 31, 2016

(54) HYBRID DUAL ENERGY IMAGING AND BONE SUPPRESSION PROCESSING

(71) Applicant: Carestream Health, Inc., Rochester, NY (US)

(72) Inventors: Xiaohui Wang, Pittsford, NY (US); Zhimin Huo, Pittsford, NY (US); David H. Foos, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 14/078,839

(22) Filed: Nov. 13, 2013

(65) Prior Publication Data

US 2014/0140479 A1     May 22, 2014

Related U.S. Application Data

(60) Provisional application No. 61/728,821, filed on Nov. 21, 2012.

(51) Int. Cl.
*A61B 6/00*            (2006.01)

(52) U.S. Cl.
CPC ............... *A61B 6/482* (2013.01); *A61B 6/505* (2013.01); *A61B 6/5205* (2013.01)

(58) Field of Classification Search
USPC ......... 378/98.12, 62; 382/132, 224, 264, 256, 382/275
See application file for complete search history.

(56) References Cited

U.S. PATENT DOCUMENTS

| 7,085,407 | B2 | 8/2006 | Ozaki | |
| 2004/0101104 | A1* | 5/2004 | Avinash | A61B 6/032 378/98.12 |
| 2007/0019852 | A1 | 1/2007 | Schildkraut et al. | |
| 2008/0011960 | A1* | 1/2008 | Yorkston | G01T 1/2018 250/370.09 |
| 2009/0060366 | A1 | 3/2009 | Worrell et al. | |
| 2009/0060372 | A1 | 3/2009 | Maton et al. | |
| 2009/0190818 | A1 | 7/2009 | Huo | |
| 2009/0214099 | A1 | 8/2009 | Merlet | |
| 2009/0285361 | A1* | 11/2009 | Akahori | G06K 9/6206 378/98.11 |
| 2009/0290779 | A1 | 11/2009 | Knapp et al. | |
| 2010/0086185 | A1* | 4/2010 | Weiss | B60R 25/00 382/131 |
| 2013/0108135 | A1 | 5/2013 | Huo et al. | |

OTHER PUBLICATIONS

Frank Vogelsang et al., Model based analysis of chest radiographs, Medical Imaging 2000: Image Processing, Proceedings of SPIE, vol. 3979, 2000, pp. 1040-1052.

(Continued)

*Primary Examiner* — Phillip A Johnston
*Assistant Examiner* — Hsien Tsai

(57) ABSTRACT

A method for obtaining a digital chest x-ray image of a patient, executed at least in part by a computer system, acquires a standard dose radiographic image and a reduced dose radiographic image, wherein the standard dose radiographic image and reduced dose radiographic images are obtained at peak kilovoltage values that differ by at least 10 kVp. A bone-enhanced image is formed by combining data from the standard dose radiographic image and reduced dose radiographic images and bone structure is segmented from the bone-enhanced image. A processed image is formed by suppressing bone contrast from the standard dose radiographic image according to the segmented bone structure. The processed image is displayed, stored, or transmitted.

20 Claims, 13 Drawing Sheets

(56) References Cited

OTHER PUBLICATIONS

Frank Vogelsang et al., Detection and Compensation of Rib Structures in Chest Radiographs for Diagnose Assistance, Proceedings of SPIE, 3338, 1998, pp. 774-785.

Kenneth Suzuki et al., Image-Processing Technique for Suppressing Ribs in Chest Radiographs by Means of Massive Training Artificial Neural Network (MTANN), IEEE Transactions on Medical Imaging, vol. 25, No. 4, Apr. 2006, pp. 406-416.

C.S. Moore et al., Investigation of optimum X-ray beam tube voltage and filtration for chest radiography with a computed radiography system, The British Journal of Radiology, vol. 81, Oct. 2008, pp. 771-777.

M. Loog et al., Filter learning: Application to suppression of bony structures from chest radiographs, Medical Image Analysis, vol. 10, 2006, pp. 826-840.

John M. Boone et al., A comparison of mono- and poly-energetic x-ray beam performance for radiographic and fluoroscopic imaging, Med. Phys., vol. 21, No. 12, Dec. 1994, pp. 18531863.

* cited by examiner

HYBRID DUAL ENERGY IMAGING AND BONE SUPPRESSION PROCESSING

CROSS-REFERENCE TO RELATED APPLICATIONS

Priority is claimed from U.S. Provisional Patent Application Ser. No. 61/728,821, filed Nov. 21, 2012 entitled "HYBRID DUAL ENERGY IMAGING AND BONE SUPPRESSION PROCESSING" in the names of Wang et al. and incorporated herein in its entirety.

FIELD OF THE INVENTION

The invention relates generally to the field of radiographic imaging and more particularly to methods for improving image quality and exposure settings for chest x-ray imaging.

BACKGROUND OF THE INVENTION

The chest x-ray is used for detecting a number of patient conditions and for imaging a range of skeletal and organ structures. Radiographic images of the chest are useful for detection of lung nodules and other features that indicate lung cancer and other pathologic structures and other life-threatening conditions. In clinical applications such as in the Intensive Care Unit (ICU), chest x-rays can have particular value for indicating pneumothorax as well as for showing tube/line positioning and other clinical conditions.

The chest region includes a wide range of tissues, ranging from rib and other bone structures to the lung parenchyma. This greatly complicates the task of radiographic imaging for the chest region, since the different types of bone and tissue materials differ widely in density. Optimization techniques that have been developed for chest imaging employ making a number of compromises to provide a suitable signal-to-noise ratio (SNR) and sufficient contrast-to-noise ratio (CNR) for soft tissue. In spite of these image processing techniques, the broad range of densities and structures leads to what has been termed "anatomical clutter", making it particularly challenging to interpret chest x-ray images in many cases.

Chest radiographs are often used to examine the lung parenchyma, for which tissue/air contrast is an important feature. As indicated in published work either based on Monte Carlo simulations (such as, for example, in the article entitled "A comparison of mono- and poly-energetic x-ray beam performance for radiographic and fluoroscopic imaging," J. M. Booth et al, *Medical Physics*, vol 21, no. 12, 1994) or based on experimental measurements (such as in "Investigation of optimum X-ray beam tube voltage and filtration for chest radiography with a computed radiography system,", C. S. Moore, *The British Journal of Radiology*, vol. 81, 2008), the optimal kV range for soft-tissue and air contrast, for average-sized adult patients, is from 60 to 80 kVp using poly-energetic x-ray beams at the same effective patient dose. However, this is rarely used in practice. Instead, the x-ray exposure technique that is routinely used for in-room posterior-anterior (PA) view chest radiography specifies 110 kVp to 130 kVp. This higher kVp range is used because it helps to reduce bone contrast. In chest images, the bone contrast from the surrounding rib cage is reduced in order to allow better visibility of the underlying tissue. The Monte Carlo simulation described by Booth et al. indicates that, with increasing exposure kVp, bone contrast decreases at a faster rate than soft tissue contrast decreases. Therefore, acquiring chest images at higher kVp helps to mitigate the bone contrast while still maintaining a reasonable level of soft tissue contrast. However, as a result of this compromise, the contrast of the lung parenchyma is less than optimal. This complicates the job of diagnosis and makes it more likely that image features be misinterpreted.

Another aspect of using higher kVp levels for chest imaging relates to increased x-ray scatter. Scatter reduces image detail contrast and increases noise levels, both of which hinder diagnostic accuracy. X-ray anti-scatter grids are frequently used to reduce scattering, but have negative effects as well. Grids of higher ratios are employed at higher energy levels, increasing the amount of incident exposure that is needed to compensate the exposure loss, but at the expense of increased patient absorbed dose.

A further issue relates to the need for imaging both bone and soft tissue in some patients. Booth et al indicate that 50 kVp is an optimal setting for bone contrast. Since standard chest exams are performed at higher kVp, typically around 120 kVp as noted earlier, rib bone contrast is greatly reduced in the images obtained, with correspondingly reduced bone detail conspicuity for diagnosis. Thus, patients for whom both thoracic bones and lung regions are examined often undergo two separate examinations, one radiograph taken at the 120 kVp level, another taken at 70 kVp. Because multiple views may be desired, a patient may need to undergo more than two exposures for a chest exam, one set of exposures optimized for lung fields, the other optimized for thoracic bones. Thus, the need to image at two different kVp levels can directly translate to double or even triple the exposure dose to the patient.

The use of lower energy x-ray photons helps to maximize soft-tissue and bone contrast in chest radiographs, but there can be negative effects if not applied appropriately. Lower energy photons become absorbed quickly by human tissues as the poly-energetic x-ray beam penetrates the patient. The negative impact of absorption is two-fold: 1) potentially increased absorbed dose to the patient, and 2) "beam hardening" effects. Beam hardening essentially modifies the x-ray spectrum at different positions in the image and reduces the effectiveness of radiation that is otherwise optimized for chest imaging. This effect becomes worse as patient size increases.

Dual energy (DE) imaging has been used as an alternative method for reducing the anatomical clutter that is typical of the chest x-ray. In DE imaging, low and high kVp exposures follow each other in close succession, so that their results can readily be combined without extensive registration techniques. No segmentation of rib features is needed; a weighted subtraction, pixel-by-pixel, can provide a degree of rib suppression that yields an image that can be more accurately interpreted.

There are some aspects to conventional DE imaging and resulting recombination techniques, however. One aspect of DE imaging relates to high dose levels, often as much as 1.5 to 2.5 times higher than standard chest x-ray exposures. Motion artifacts often result, leading to misregistration due to breathing, heartbeat, and other movement of the patient.

Even where motion artifacts are minimal, however, overall image quality is compromised in DE image processing. In dual energy imaging, the soft-tissue contrast-to-noise ratio (CNR) in the clear lung region (e.g., regions without any overlaying bone structures) is compromised in the soft tissue image during the subtraction operation between the high and low energy images. Since the clear lung region has no bone structures, it is desirable to maintain the CNR of the originally captured data.

Another technique that has been used for chest x-ray imaging is rib suppression. Rib suppression processing has been used to reduce rib effects without introducing additional radiation dose by operating on a standard chest x-ray image in regions where there are overlapping bone structures. However, the performance of rib suppression processing depends on the segmentation accuracy of the bone analysis algorithm. Because the image analysis is performed on the standard chest image, and soft-tissue and bone structures overlay each other, it can be very difficult to separate the bones from the underlying soft tissue structure. In some situations, one or more rib bones, or sections of rib bones, are missing from the segmentation analysis and are, therefore, not accurately suppressed. In some situations, some of the soft tissue structures may be mistakenly identified as bone structures, therefore being negatively suppressed.

Thus it can be seen that even though various approaches have been used to mitigate anatomical clutter in chest x-ray images, each of these approaches have their limitations. There is a need for solutions that provide the practitioner with chest x-ray images with reduced dose to the patient while at the same time exhibiting good contrast across the whole image.

SUMMARY OF THE INVENTION

Embodiments of the present invention address the need for improved imaging parameters and processing for chest x-rays. Advantageously, embodiments of the present invention provide a method for chest x-ray imaging using technique settings that reduce patient exposure and provide improved contrast for lung tissue.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to at least one aspect of the invention, there is provided a method for obtaining a digital chest x-ray image, the method executed at least in part by a computer system and comprising: acquiring a standard dose radiographic image and a reduced dose radiographic image, wherein the standard dose radiographic image is obtained at a peak kilovoltage value that is at least 10 kVp lower than the reduced dose radiographic image; forming a bone-enhanced image by combining data from the standard dose and reduced dose radiographic images; segmenting bone structure from the bone-enhanced image; forming a processed image by suppressing bone contrast from the standard dose radiographic image according to the segmented bone structure; and displaying the processed image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
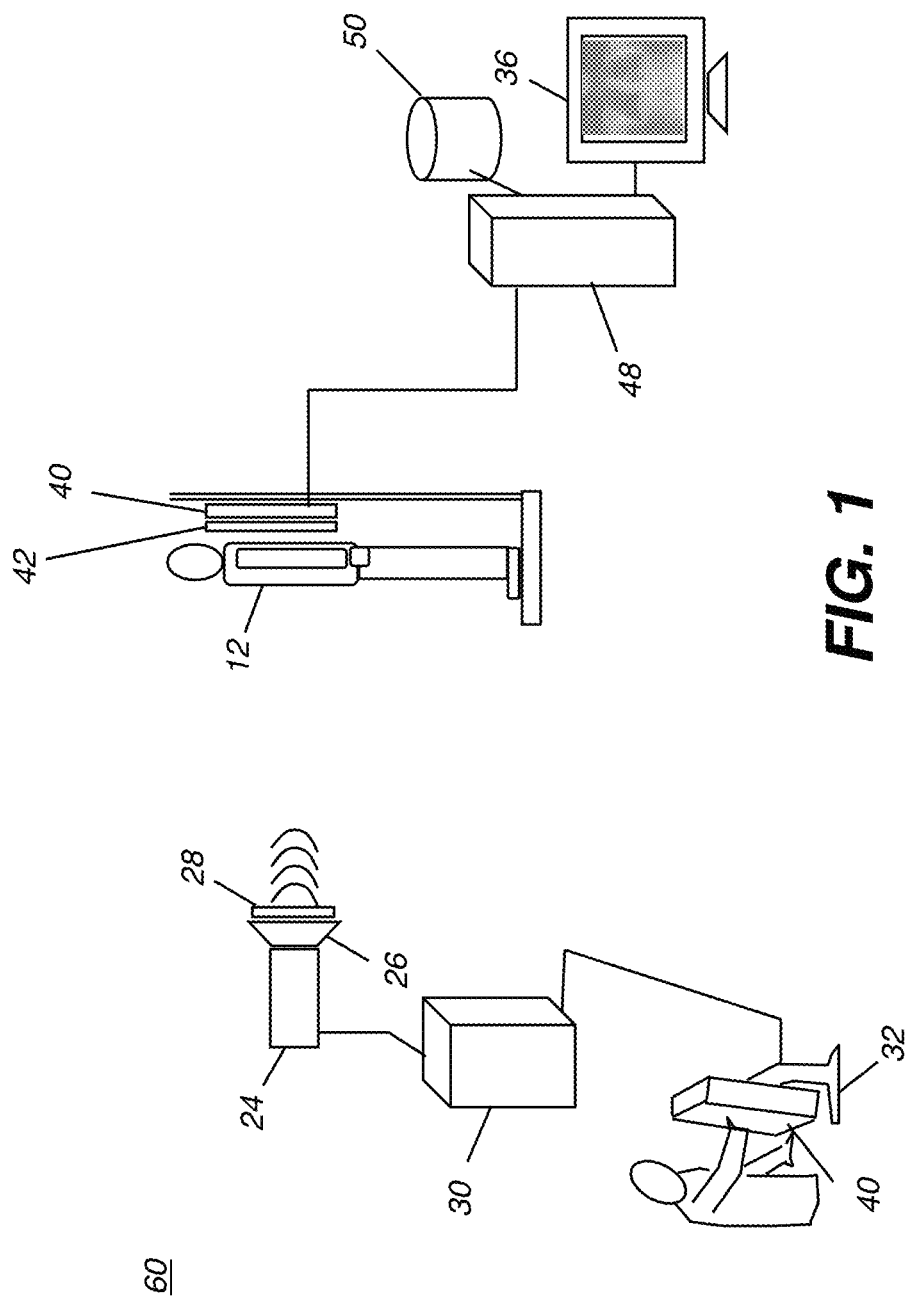
FIG. 1 is a schematic diagram of an imaging apparatus for providing chest x-ray imaging of a patient according to an embodiment of the present invention.

The following is a detailed description of the preferred embodiments of the invention, reference being made to the drawings in which the same reference numerals identify the same elements of structure in each of the several figures.

Where they are used, the terms "first", "second", "third", and so on, do not necessarily denote any ordinal or priority relation, but may be used for more clearly distinguishing one element or time interval from another.

In the context of the present disclosure, the term "effective dose" relates to a tissue-weighted sum of equivalent dose, a measure of absorbed dose, in specified tissues and organs of the body. Effective dose is typically quantified in sieverts (Sv). The term "standard dose" relates to standard values of effective dose that apply for a particular type of exam and is determined, in part, by practices followed at a particular radiographic imaging site.

In the context of the present disclosure, a digital chest x-ray can be obtained from a digital receiver (DR) or computed radiography (CR) receiver.

In the context of the present disclosure, the term "segmentation" has the broad meaning that is generally understood by those skilled in the image processing arts. The act of segmenting the image partitions the image content in some way so that one or more sets of pixels are grouped according to the feature(s) they represent. Thus, for a chest x-ray for example, lung segmentation defines those portions of the image that represent lung tissue for a patient.

Embodiments of the present invention are directed to the problem of obtaining chest x-ray images using a set of x-ray setup parameters, also termed techniques, that differ from those conventionally used in conventional chest radiography and from those used in dual-energy chest radiography. Embodiments of the present invention apply a hybrid technique that combines some of the benefits of dual-energy imaging, but with reduced exposures compared to conventional DE imaging, and adds some of the advantages of rib suppression techniques in order to provide improved imaging of the underlying lung tissue.

As noted in the background material described previously, one factor that has caused radiography personnel to use higher peak kilovoltage (kVp) levels than are optimal for imaging the lung parenchyma relates to the need for reduced rib contrast. One aspect of the present invention uses a rib contrast suppression method described in detail in commonly assigned U.S. patent application Ser. No. 13/527,629 filed Jun. 20, 2012 in the names of Huo et al, entitled, "RIB SUPPRESSION IN RADIOGRAPHIC IMAGES" to Huo, incorporated herein by reference.

In the process described in the Huo application, a lung segmentation process is followed by a rib detection process in which rib content is separated from non-rib image content. A rib labeling step follows, with classification of the rib content, grouping likely rib pixels into corresponding categories and helping to remove false positives. Some amount of prior knowledge of rib structures, such as shape and general direction, is used, along with morphological filtering. Characteristics such as gradient orientation and shape are then used for rib edge segmentation, in which edge portions of the ribs are identified. Finally, rib subtraction is used to subtract rib edges from the chest x-ray image to provide a rib-suppressed x-ray image.

It should be noted that alternate methods for rib contrast suppression can be used, including those using modeling or based on other features. Rib bone contrast suppression, when properly applied, helps to reduce the impact of rib structures on the surrounding tissue, so that the lung parenchyma can be more readily visible. Significantly, using rib contrast suppression allows the reduction of kVp levels used for imaging, so that values lower than 120 kVp can be used to provide a suitable chest x-ray image. This also helps to reduce overall noise levels, improving image contrast.

Referring to FIG. 1, there is shown a schematic diagram of an imaging apparatus 60 for providing chest x-ray imaging of a patient 12 according to an embodiment of the present invention. An x-ray tube 24 provides the needed exposure radiation for imaging, under the control of control circuitry 30 that has an operator console 32 for entry of setup and operation commands from the technician. X-ray tube 24 has a collimator 26 that controls the angular and spatial distribution of radiation that is provided. A filter 28 is provided at the output of x-ray tube 24. Filter 28 positioning is typically controlled by control circuitry 30. Imaging apparatus 60 uses a single DR detector 40 that has a grid 42 for scatter compensation. A DR imaging processor 48 obtains the digital data from DR detector 40 and performs the image processing steps for the obtained image data, including rib contrast suppression. A display 36 in communication with DR imaging processor 48, or other output device, then displays each obtained image. A computer-accessible memory 50 enables processing and storage of the obtained and processed image data.

Figure 2:
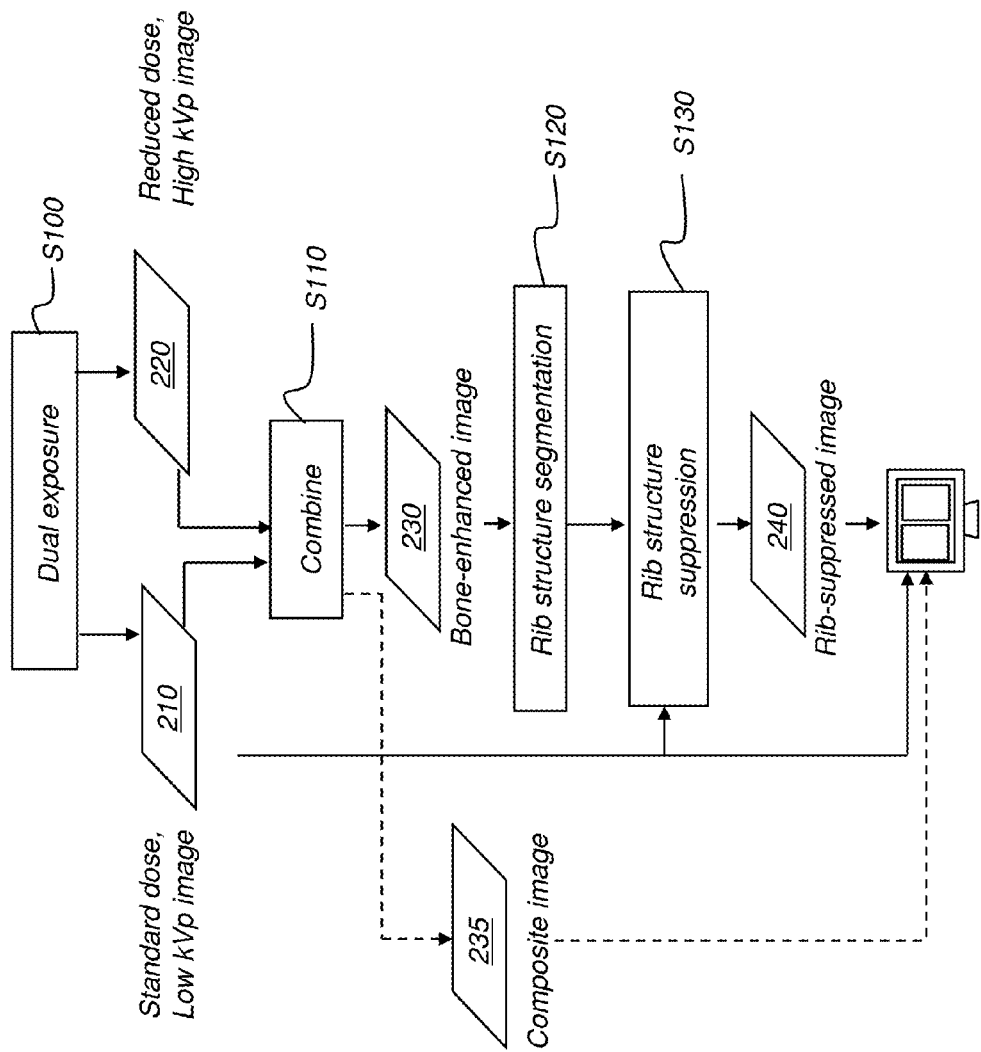
FIG. 2 is a logic flow diagram that shows a sequence of steps for image processing according to an embodiment of the present invention.

The logic flow diagram of FIG. 2 shows a sequence of steps for processing a chest x-ray image according to an embodiment of the present invention. In an exposure step S100, two images are acquired, in rapid succession, similar to the sequence used for dual-energy imaging, but differing from conventional dual-energy imaging with respect to exposure levels. A standard dose, low-energy image 210 is acquired at an exposure peak kilovoltage setting of about 60-90 kVp and at standard effective dose to the patient, using dose levels conventionally used in conventional chest imaging for the patient. A reduced dose, high-energy image 220 is acquired at 100-160 kVp and at low effective dose to the patient, such as at about 5% to 50% of the standard effective dose used in conventional chest imaging. Standard and reduced dose images 210 and 220 can be acquired in either order. A combination step S110 combines the low-energy standard dose image 210 and the high-energy reduced dose image 220 to generate a bone-enhanced image 230 and, optionally, a composite image 235. Combination step S110 can use a weighted subtraction or other suitable combination method for generating bone-enhanced image 230. In a weighted subtraction method, each pixel is assigned a new value C for the bone-enhanced image 230 using:

$$A - (B * \text{factor}) = C$$

Wherein A is the pixel value from the low energy image 210;
B is the pixel value from the high-energy image 220;
factor is an empirically determined value.
Optional composite image 235 is generated by addition of the image content for images 210 and 220.

Continuing with the sequence of FIG. 2, a rib structure segmentation step S120 is then executed, generating a rib-suppressed image 240 as described in more detail in subsequent figures. Rib structure segmentation step S120 detects and segments the bone structure using the bone enhanced image 230. Rib structure suppression step S130 forms a processed, rib-suppressed image 240 by suppressing bone contrast from the standard dose, low energy image 210 according to the segmented bone structure from the bone-enhanced image 230. Suppressing the bone contrast can include conditioning the magnitude of detected bone edges. This can involve any of a number of conventional image processing techniques, including filtering, for example. Processing step S130 calculates a new value for each pixel in the low energy image 210 that was identified as having rib content, weighted according to the intensity of the rib content, using pixel combination techniques familiar to those skilled in the image analysis and processing arts. Rib-suppressed image S240 displays, along with the standard dose, low kVp image. Simultaneous display of processed and standard images allows comparison of the rib suppressed image with the standard image. Composite image 235 can optionally also be displayed along with either or both images 240 and 210.

Radiation at different wavelengths is absorbed at different levels by human tissue. In general, higher energy photons penetrate and pass through the imaged subject more effectively and are less likely to be absorbed than are photons of lower energy. For this reason, conventional practices for chest imaging of adults set energy levels above or well above 90 kVp, such as at 120 kVp, for example. In the context of the present disclosure, the term "standard dose" refers to a level of exposure that is conventionally used for a particular type of exam. The standard dose that applies for any particular case varies based on factors such as patient size, technique settings, and other variables and is often determined using an Automatic Exposure Control (AEC) device that terminates exposure when a predetermined amount of energy has been received at the detector. Use of the standard dose for an exam is determined to provide sufficient image quality for diagnostic purposes. Dose calculation for a particular type of exam is typically performed using a phantom and the results used to standardize procedures at an imaging site.

As is known to those skilled in radiography, various information is used in order to compute effective dose for a particular patient, according to national and local standards and practices observed at a particular imaging site. Effective dose varies with factors such as the relative sensitivity of various types of tissue to radiation. Tissue weighting factors are provided that vary according to the sensitivity of various organ types. The weighting factor for reproductive organs, for example, is several times higher than the weighting factor for bone structures. Effective dose for chest x-ray imaging varies somewhat with patient size.

Applicants have recognized that improvements are desired for methods using rib edge detection to identify rib structures that can then be suppressed in the x-ray image. There is a desire, for example, to adapt rib detection methods to individual patient images. Methods using template or function-fitting of the detected rib edge have limitations for successfully characterizing large variations in the shape of ribs as well as limitations related to image quality, especially when foreign objects, e.g., tubes/lines and other devices, are captured in the chest images.

Conventional rib detection techniques typically first locate rib/line edges, then use rib edge information to identify rib structures that lie between the rib edges. The inventors have found results from this conventional approach to be disappointing, often failing to provide accurate enough information on rib structures for acceptable levels of rib suppression. Embodiments of the present invention address the problem of rib suppression in a different manner, by detecting rib regions first, then, once features of individual rib structures have been identified, more accurately and robustly locating rib edges. This approach allows the complete rib structure to be identified and its affect on image content more accurately profiled than has been achieved using conventional methods. Once the full structure of the ribs can be identified, instead of merely tracing rib edges or outline features, processing of the image content can be more accurately performed.

Figure 3:
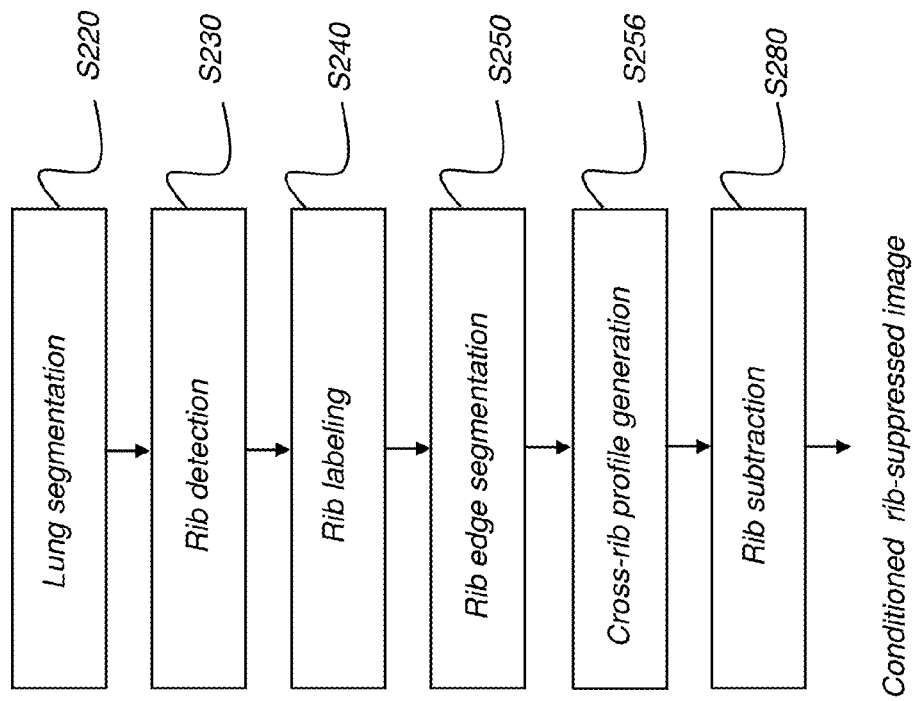
FIG. 3 is a logic flow diagram showing a sequence for automated rib suppression consistent with an embodiment of the present invention.

The logic flow diagram of FIG. 3 shows a sequence for automated rib detection and suppression that can be used as part of step S120 in FIG. 2, consistent with an embodiment of the present invention for chest x-ray image processing. In a lung segmentation process S220, the lung and rib cage portions of the image are segmented, thus extracting the lung region of interest from the image. A number of approaches to lung segmentation are known and have been proposed, including, for example, that described in U.S. Pat. No. 7,085,407 entitled "Detection of Ribcage Boundary from Digital Chest Image" to Ozaki that employs landmark detection and other utilities to detect the boundaries of the rib cage. Other methods for lung detection and segmentation include methods that detect the spine structure and use a bounding box for coarse detection, with subsequent processing for more closely identifying the boundaries of the lung or rib cage. Neural network-based logic can also be employed for generating a pixel-based lung segmentation. Boundary smoothing can also be employed, such as by using morphological filtering or other suitable processing technique, for example.

Continuing with FIG. 3 processing, with the lung region of interest or area including the lungs identified, a rib detection step S230 follows, in which structural information about the rib features is used in conjunction with image pixel intensities to separate likely rib content from non-rib image content. This step helps to eliminate from processing the image content that is not obstructed by rib features and has been found to provide improved results. Further processing of the candidate rib content is executed in a rib labeling step S240 that groups and organizes the detected rib contents. In rib labeling step S240, classification of the rib content groups likely rib pixels into corresponding categories for labeling as part of individual ribs, labels these pixels as part of the rib content of the image, and helps to remove false positives from rib detection step S230. Position, shape information, and gradient are used, for example, to help eliminate false positives. Processing in step S240 provides for classifying pixels into one or more of multiple ribs, by using some amount of prior knowledge of rib structures, such as shape, position, and general direction, and by applying morphological filtering. Among features that have been found to be particularly useful for rib classification are rib width and position, including percentage of pixels initially determined to be part of a rib feature. Other features could similarly be extracted and used for false-positive removal. Rib labeling in labeling step S240 alternately calculates a medial axis for one or more ribs to generate a skeletal image for validating rib detection and for subsequent processing including rib modeling for retrieving missing or missed-labeled ribs or portion of ribs. The skeletal image has medial axis information and, optionally, other anatomical data relevant to rib location.

Characteristics such as gradient orientation and shape for the labeled rib content can then be used for subsequent processing in a rib edge segmentation step S250. In rib edge segmentation step S250, edge portions of the ribs are identified, and this identification is refined using iterative processing. Guided growth processing may alternately be used to enhance rib edge detection. A cross rib profiling step S256 generates a cross rib profile that provides values for rib compensation along the detected ribs. Finally, a rib subtraction step S280 is executed, subtracting rib edges and values from the rib profile from the chest x-ray image, to condition the image and provide a rib-suppressed x-ray image as the conditioned image for display. Other types of conditioning can be used for combining the detected rib information with the original x-ray image to generate a rib-suppressed image for display or for further analysis.

Figure 4:
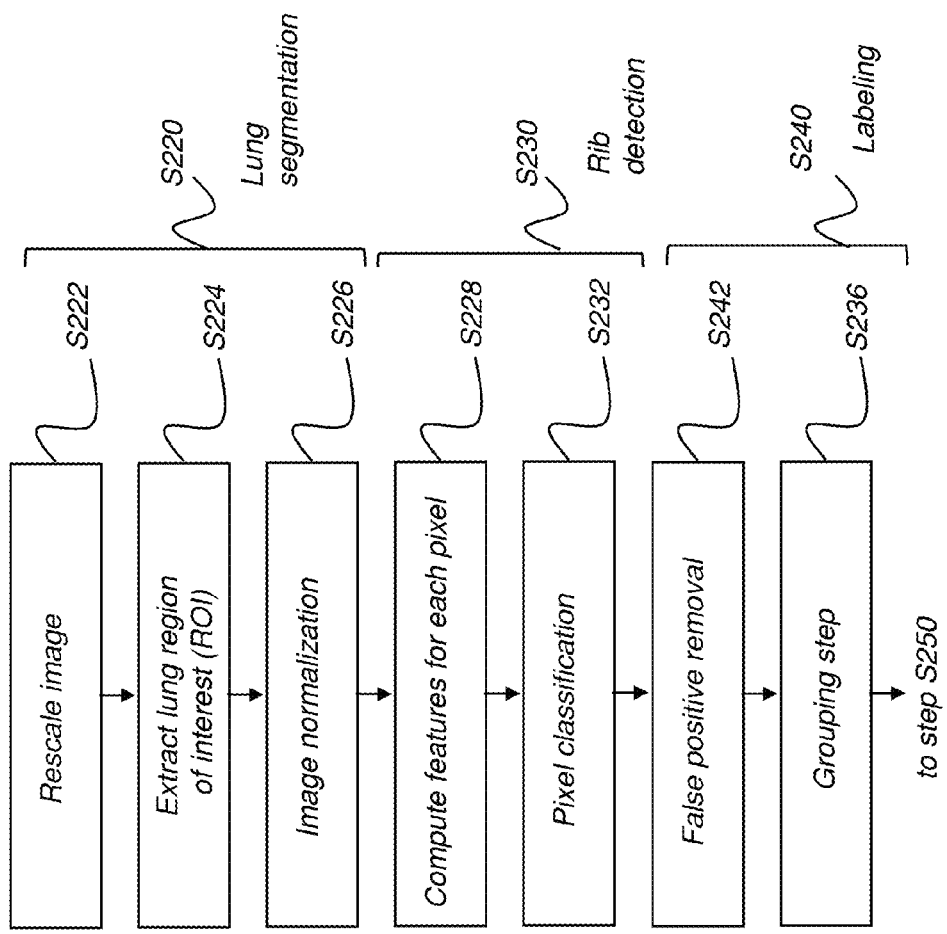
FIG. 4 is a logic flow diagram that shows processing that is performed in lung segmentation and rib detection.

The logic flow diagram of FIG. 4 shows processing that is performed in lung segmentation process S220, rib detection step S230, and labeling step S240, and shows how the results of this processing are used. In an optional scaling step S222, the image can be scaled to a lower resolution in order to speed subsequent processing. An extract ROI step S224 helps to generate position features information for more accurate definition of the region of interest (ROI). An image normalization step S226 then provides normalized information on image features, consistent with multiple images.

Rib detection step S230 determines, for pixels in the region of interest, whether or not each pixel corresponds to a rib feature. Rib detection step S230 has a features computation step S228 that computes features for each pixel, such as providing Gaussian derivative features information and position information, for example. Next, as part of rib detection step S230, a pixel classification step S232 determines whether each pixel within the lung region is a rib or non-rib pixel. Classifier techniques such as artificial neural network, supporting vector machine or random forests that are well known in the art can be used to perform the pixel classification.

In this sequence, labeling step S240 is also shown in more detail. A false positive removal step S242 executes for identifying individual ribs. False-positive pixels are first removed as part of this processing. A subsequent grouping step S236 then determines whether or not one or more groups of detected pixels can themselves be grouped together as one individual rib, based on factors such as positional relationship, connectedness and adjacence, gradient features, and the position relative to the central axis of individual groups. These ribs can be labeled according to rib pattern. Global rib modeling, based on ribs that have already been labeled and known anatomical relationships, can be used to detect a missing rib from the previous steps.

Figure 5:
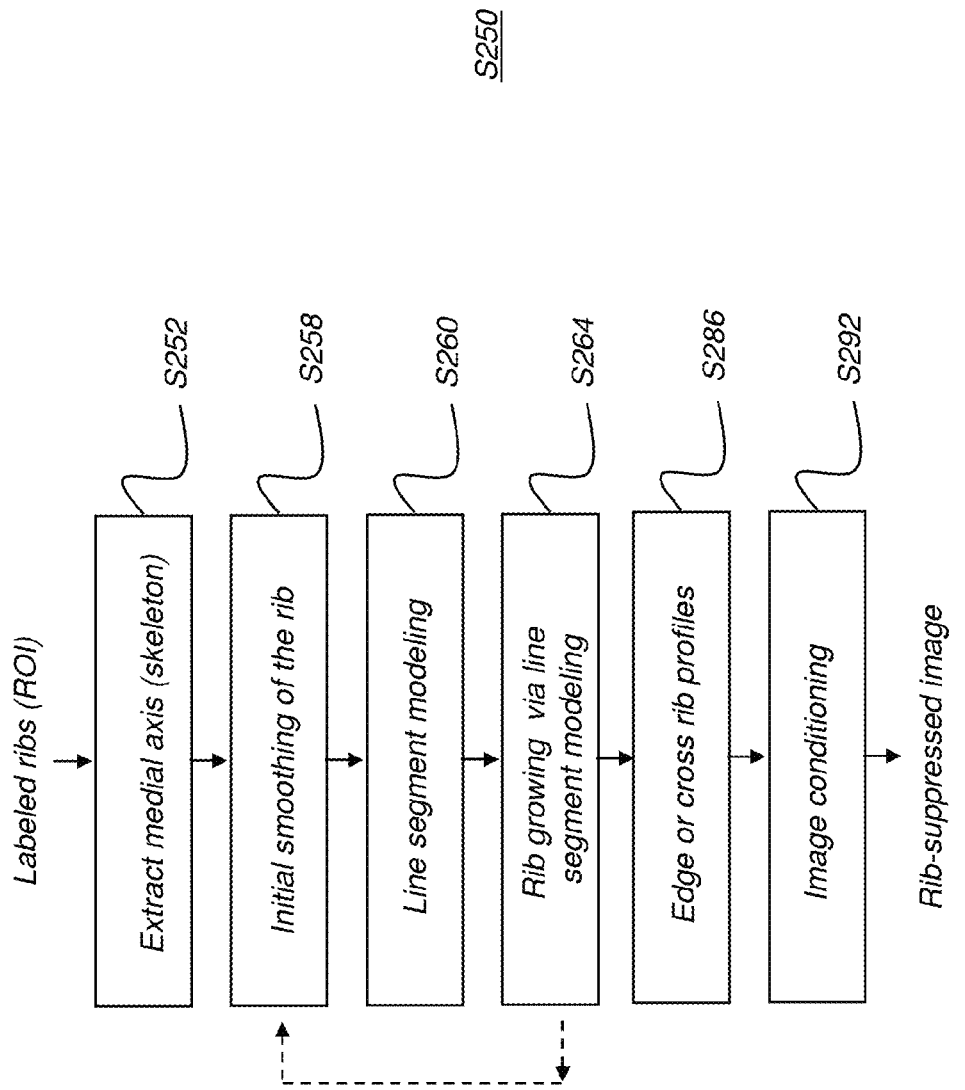
FIG. 5 is a logic flow diagram that shows iterative processing that is performed for each detected or labeled rib as part of rib edge segmentation.

The logic flow diagram of FIG. 5 shows iterative processing that is performed for each detected or labeled rib, after the processing described with respect to FIG. 2, as part of rib edge segmentation S250 (FIG. 3). The input to this processing is the set of labeled ribs. A medial axis extraction step S252 obtains the medial axis of each rib. An initial smoothing step S258 performs any necessary fitting to smooth rib edges, according to the extracted medial axis. As part of smoothing step S258, the smoothed boundaries provide a starting point for more closely approximating rib edges. Using the smoothed rib contour, one or more line segments for the upper or lower rib boundaries are generated as initial rib edge candidates. Next, one or more additional line segment candidates for each segment are generated based on calculated gradients or other features. A set of the best-fit edge candidates for the upper and lower rib edge is selected, using optimization of a model based on factors such as edge gradients, rib width, line segment smoothness, and rib shape constraints.

Continuing with the sequence of FIG. 5, a rib growing step S264 continues the line segment optimization process of modeling step S260 to extend existing line segments and merging disconnected line segments as they are detected or extrapolated from existing segments. A growing algorithm is useful where segments of the ribs are foreshortened or missing. As part of the growing algorithm, existing segments are aligned according to an anatomy model. Segments are iteratively extended and tested to determine whether or not growth is completed. Segment growth can also use edge extension techniques such as those employed for tubing detection and described in commonly assigned, copending U.S. Patent Application No. 2009/0190818 entitled "Computer-Aided Tubing Detection" by Huo.

Repeated iteration of the sequence of steps S258, S260, and S264, as many times as needed, helps to improve the collected rib profiles that are generated and provided in a cross-rib profile generation step S286, so that rib data that is combined with the image data in image conditioning step S292 more accurately characterizes the rib content.

Figure 6B:
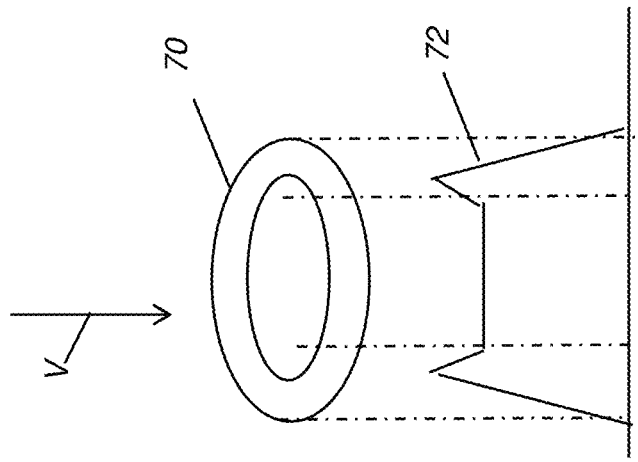
FIG. 6B is a schematic diagram that shows how a cross rib profile for a chest x-ray is generated.
Figure 6A:
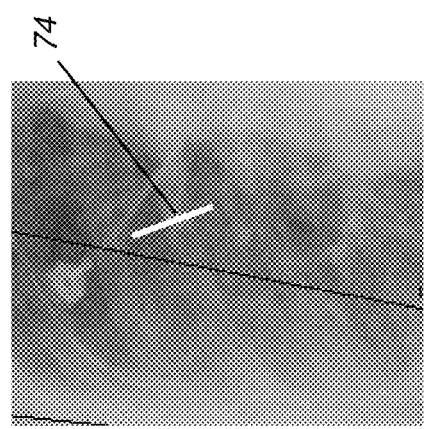
FIG. 6A shows a section of a rib with an identified portion for generating a rib profile in a chest x-ray image.

FIGS. 6A and 6B show how a cross rib profile is generated and its relationship to the chest x-ray image. In FIG. 6A, a line 74 shows the basic direction over which the profile is obtained, across the rib in a cross-sectional manner. In FIG. 6B, a rib 70 is shown schematically in cross section, representing a bony shell and a soft interior portion. A profile 72 shows how rib 70 affects image data, with peak values along the edges. X-rays are generally incident in the direction indicated V in this figure.

Profile 72 is generated using known characteristics of the rib in the chest x-ray. One method for providing rib profile 72 is to apply a low-pass filter (LPF) to the chest image and use the results of this processing to provide a cross rib profile, which is known to those skilled in image processing and analysis. An alternate method employs a model to provide an initial approximation or starting point for developing the rib profile. Using information from the model also enables rib profile information to be identified and extracted from the image itself. Whatever method is used, the usefulness of the rib profile depends, in large part, upon accurate detection of rib edges.

Those skilled in the diagnostic image analysis and processing arts are familiar with ways in which the cross rib profile can be generated and used. The article entitled "Model based analysis of chest radiographs", in *Proceedings of SPIE* 3979, 1040 (2000), by Vogelsang et al. describes Bezier curve matching to find rib edges in a chest radiograph for alignment of a model and subsequent rib shadow compensation. Interpolation and a compensation mask are employed. This article particularly describes how the cross rib profile is used as a model, and shows how six regions for vertical compensation values are identified and interpolation applied using this model.

Another article by Vogelsang et al. entitled "Detection and Compensation of Rib Structures in Chest Radiographs for Diagnose Assistance" in *Proceedings of SPIE*, 3338:774-785 (1998) describes methods for compensating for rib structures in a radiographic image. Among techniques described in this second Vogelsang et al. article are template matching and generation and selection from candidate parabolas for tracing rib edges.

Figure 7:
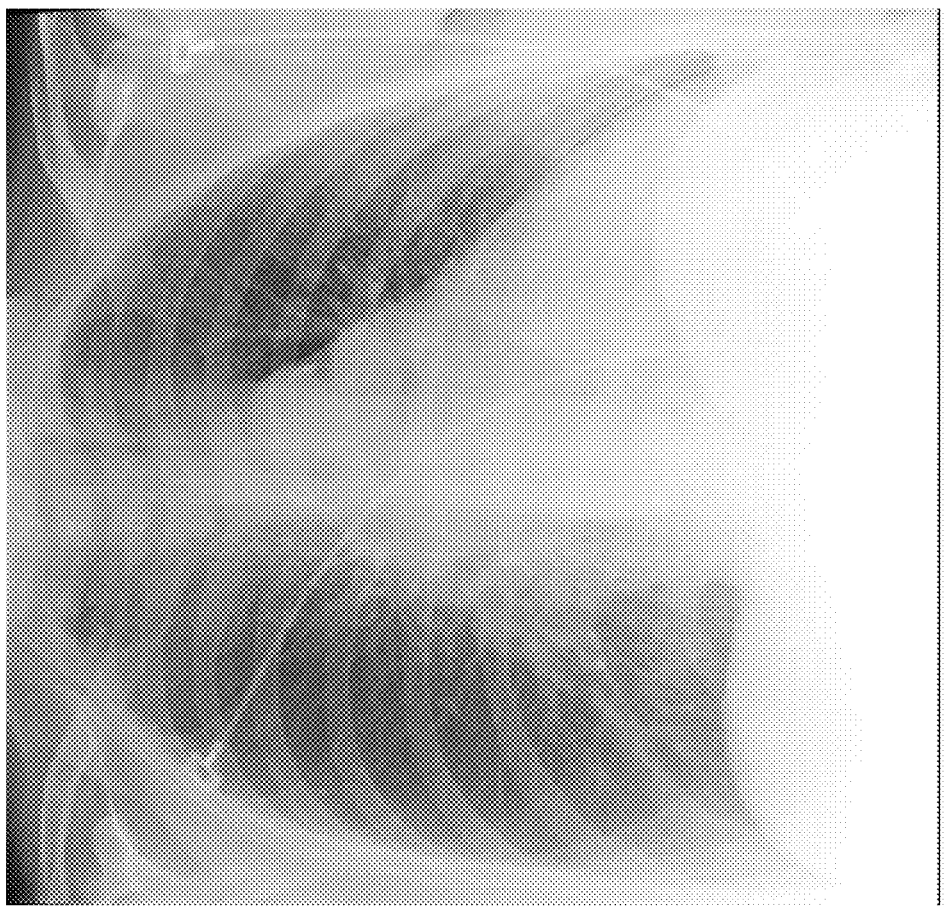
FIG. 7 shows an original chest x-ray image prior to processing for rib suppression.
Figure 8A:
FIG. 8A shows results from rib detection.
Figure 8B:
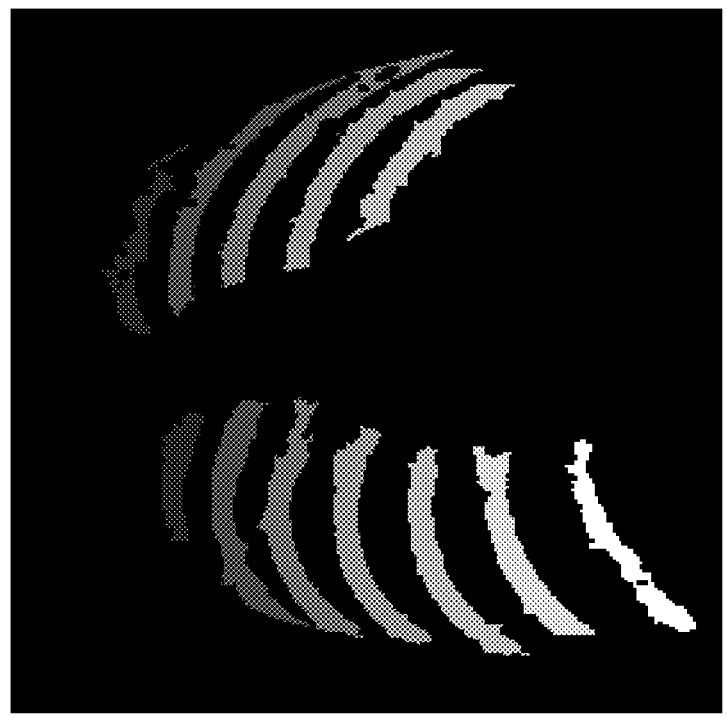
FIG. 8B shows results from rib labeling.
Figure 9:
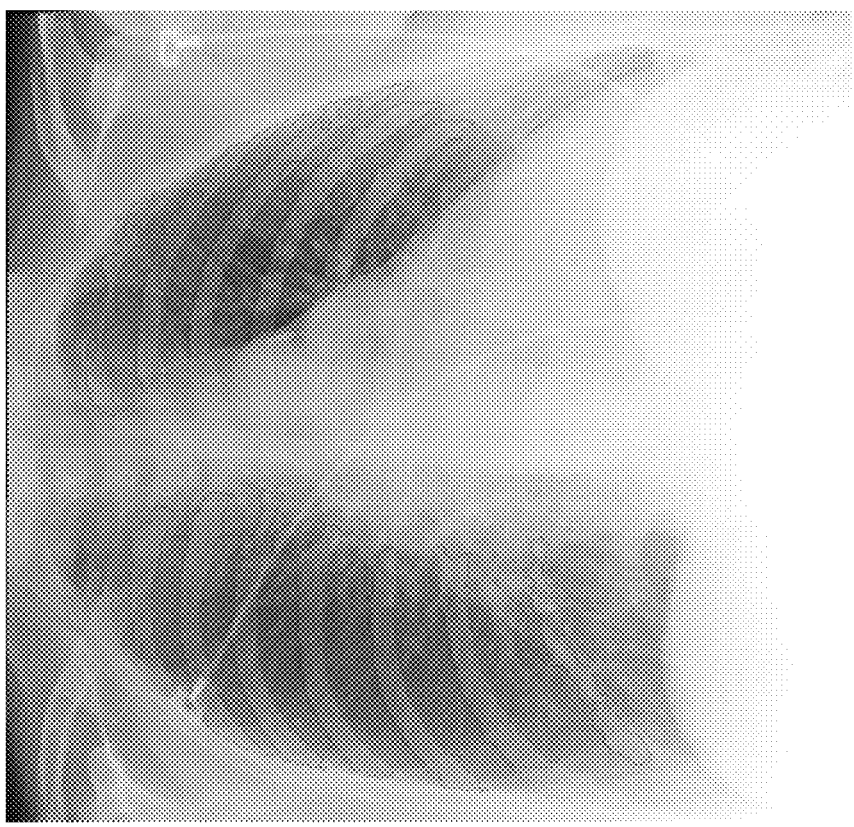
FIG. 9 shows labeled ribs overlaid onto the original image of FIG. 7.

By way of example, FIG. 7 and following show results of some of the steps of the processing sequence for rib removal according to an embodiment of the present invention. FIG. 7 shows an original chest x-ray image 38 that desires identification and removal of ribs in order to make underlying tissue more visible. FIG. 8A shows an image 44 that shows rib detection. FIG. 8B shows an image 46 following rib labeling that helps to more precisely identify the rib regions. In FIG. 9, an image 62 shows labeled ribs overlaid onto the original image 38.

Figure 10A:
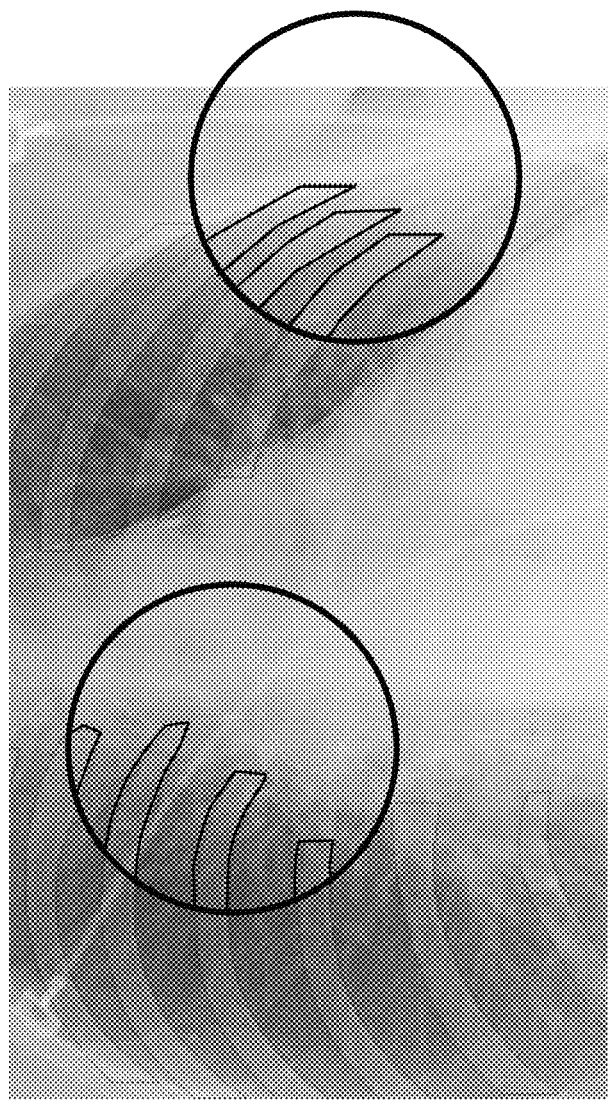
FIGS. 10A and 10B show examples of rib growing algorithms in operation.
Figure 10B:
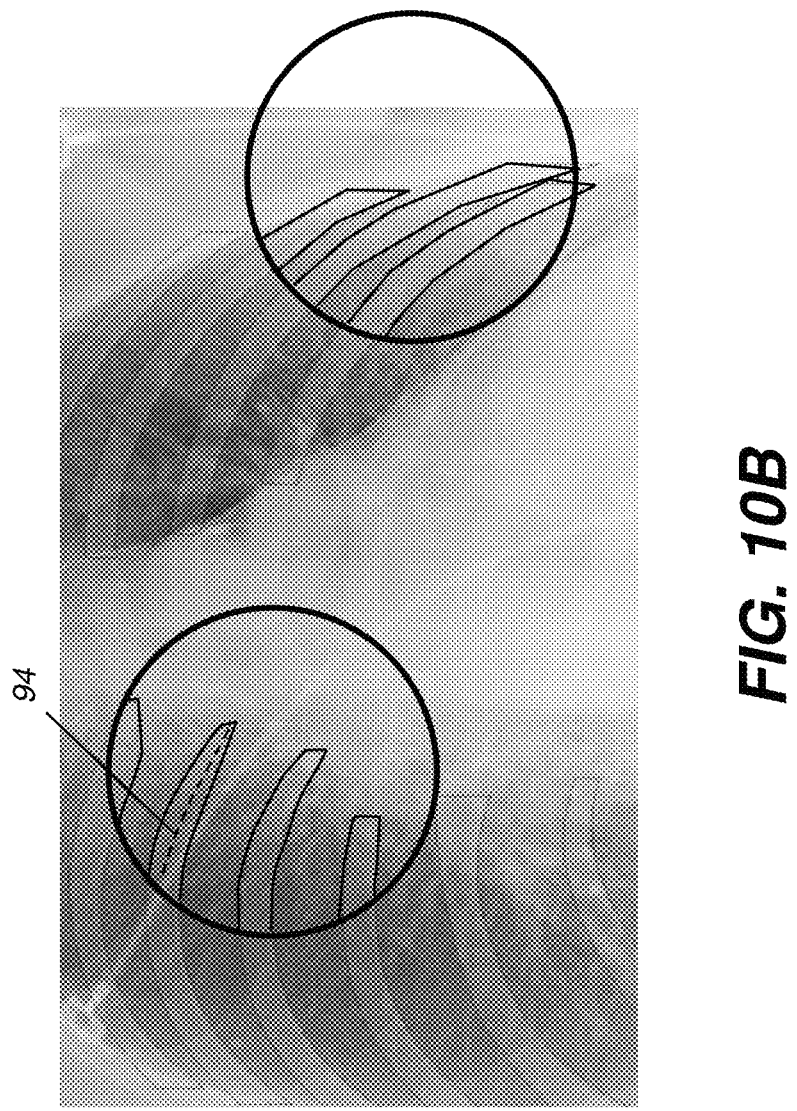

FIGS. 10A and 10B show an example of rib growing using the overlaid results of FIG. 9. Rib growing algorithms are of particular value for extending the rib curvature along the ends of the rib, where features may be unclear, and help to provide improved edge detection. In an embodiment of the present invention, rib growing algorithms follow the general curvature of a medial axis 94. FIG. 10B shows an example medial axis 94 in dashed line form.

Figure 11:
FIG. 11 shows a chest x-ray image with suppressed rib content, following a subtraction operation.

As noted previously, there are a number of methods for combining rib edge information with the final image provide a rib suppressed image, as shown in FIG. 11. Available methods for combining rib edge content include weighted subtraction, filtering, interpolation, and other methods known to those skilled in the image processing arts.

X-ray beam filtration can be used when acquiring image data in order to further separate the beam energy between the lower and higher kVp exposures of the standard and reduced dose images, using filter 28 (FIG. 1). According to one aspect of the present invention, the filtration is at least equivalent to 0.1 mm copper on the reduced dose beam.

Embodiments of the present invention help to provide more accurate detection of rib edges than available using conventional methods, such as shape modeling. In an alternate embodiment of the present invention, only the rib edge profiles are subtracted from the original image to provide rib suppression.

Compared with conventional dual-energy methods for chest x-ray processing, embodiments of the present invention acquire images at greatly reduced exposure. The total exposure can be only slightly higher than that for a single chest x-ray image and can be significantly less than the exposure in conventional DE imaging. Soft tissue contrast-to-noise ratio (CNR) is improved, as well as overall signal-to-noise ratio (SNR).

Consistent with one embodiment, the present invention utilizes a computer program with stored instructions that perform on image data that is accessed from an electronic memory. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

It is noted that there can be any of a number of alternate methods used for functions such as segmentation of ribs from other tissue in the chest x-ray image or for filtering portions of the image content.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for obtaining a digital chest x-ray image of a patient, the method executed at least in part by a computer system, comprising:
   acquiring a standard dose radiographic image and a reduced dose radiographic image, wherein the standard dose radiographic image is obtained at a peak kilovoltage value that is at least 10 kVp lower than the reduced dose radiographic image;
   forming a bone image by subtraction using the standard dose and reduced dose radiographic images;
   spatially segmenting bone structure from the bone image;
   forming a processed image by suppressing bone contrast from the standard dose radiographic image according to the spatially segmented bone structure; and
   displaying, storing, or transmitting the processed image.

2. The method of claim 1 wherein an effective absorbed dose of the reduced dose image for the patient is less than half the effective absorbed dose of the standard dose image.

3. The method of claim 1 wherein the reduced dose radiographic image is obtained at a peak kilovoltage value of 100 kVp or higher.

4. The method of claim 1 wherein the standard dose radiographic image is obtained at a peak kilovoltage value of 90 kVp or lower.

5. The method of claim 1 wherein suppressing the bone contrast comprises conditioning the magnitude of detected bone edges.

6. The method of claim 1 wherein the subtraction to form the bone image comprises performing a weighted subtraction.

7. The method of claim 1 further comprising simultaneously displaying the standard dose radiographic image and the processed image.

8. The method of claim 1 further comprising simultaneously displaying the processed image and a composite image generated by adding the standard dose and the reduced dose radiographic images.

9. The method of claim 1 further comprising applying x-ray beam filtration to further separate the beam energy between the lower and higher kVp exposures of the standard and reduced dose images.

10. The method of claim 9 wherein the filtration is at least equivalent to 0.1 mm copper on the reduced dose beam.

11. The method of claim 1 further comprising displaying a composite image formed by adding the standard dose and reduced dose radiographic images.

12. The method of claim 1 wherein the bone structure comprises one or more ribs.

13. The method of claim 1 wherein segmenting the bone structure comprises generating a cross-rib profile.

14. The method of claim 1 wherein segmenting the bone structure comprises executing a rib growing algorithm along a medial axis of at least one rib.

15. The method of claim 1 wherein segmenting the bone structure comprises adjusting segments of one or more of the detected rib edges to improve edge fitting.

16. The method of claim 1 wherein segmenting the bone structure comprises scaling the image to a reduced resolution.

17. A method for obtaining a digital chest x-ray image of a patient, the method executed at least in part by a computer system and comprising:
   acquiring a standard dose chest x-ray image and a reduced dose chest x-ray image, wherein the standard dose chest x-ray image is obtained at a peak kilovoltage value that is at least 10 kVp lower than the reduced dose chest x-ray image;
   forming a bone image by subtraction using the standard dose and reduced dose chest x-ray images;
   segmenting bone structure from the bone image;
   forming a processed image by suppressing bone contrast from the standard dose radiographic image according to the segmented bone structure; and
   displaying, storing, or transmitting the processed image and the standard dose chest x-ray image.

18. The method of claim 17 wherein the reduced dose radiographic image is obtained at a peak kilovoltage value of 100 kVp or higher.

19. The method of claim 17 wherein the standard dose radiographic image is obtained at a peak kilovoltage value of 90 kVp or lower.

20. The method of claim 17 further comprising displaying a composite image formed by adding the standard dose and reduced dose radiographic images.

* * * * *